US00PP11101P

United States Patent [19]

Stemkens

[11] Patent Number: Plant 11,101

[45] Date of Patent: Oct. 19, 1999

[54] VERBENA PLANT NAMED 'LUXENA'

[75] Inventor: Henricus G. W. Stemkens, Hoorn, Netherlands

[73] Assignee: Novartis Seeds B.V., Enkhuizen, Netherlands

[21] Appl. No.: 08/994,254

[22] Filed: Dec. 19, 1997

[51] Int. Cl.[6] ..... A01H 5/00

[52] U.S. Cl. ..... Plt./308

[58] Field of Search ..... Plt./87, 308

[56] References Cited

PUBLICATIONS

Peter Walton, Principles and Practices of Plant Science. Prentice Hall, New Jersey, pp. 29–30, 1988.

Hortus Third: A Concise Dictionary of Plants Cultivated in the United States and Canada. Bailey et al. pp. 1208–1210, 1976.

UPOV–ROM 1998/01, Plant Variety Database, GTI Jouve Retrieval Software citation for 'Luxena'.

*Primary Examiner*—Howard J. Locker
*Assistant Examiner*—Anne Marie Grünberg
*Attorney, Agent, or Firm*—Thomas Hoxie

[57] ABSTRACT

A new Verbena plant particularly distinguished by its large light blue flower, early flowering, and a semi-erect habit that becomes spreading as plant develops.

2 Drawing Sheets

BACKGROUND OF THE NEW PLANT

The present invention comprises a new distinct cultivar of Verbena, botanically known as *Verbena×hybrida*. The new cultivar is propagated from cuttings resulting from the cross of T1183 and R692 . T1183 is a white flowering Verbena having a spreading habit. T1183 is not commercially available and is not known by any synonyms. R692 is a deep blue flowering Verbena having a semi-erect habit. R692 is not commercially available and is not known by any synonyms. Neither T1183 or R692 has been patented. As a result of this cross the present cultivar was created in 1994 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on plants that were 18 weeks old, blossomed under natural light in a greenhouse. Color readings were taken in the greenhouse under ambient light. Color references are primarily to The R.H.S. Colour Chart of The Royal Horticultural Society of London.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

The Plant

Figure 1:
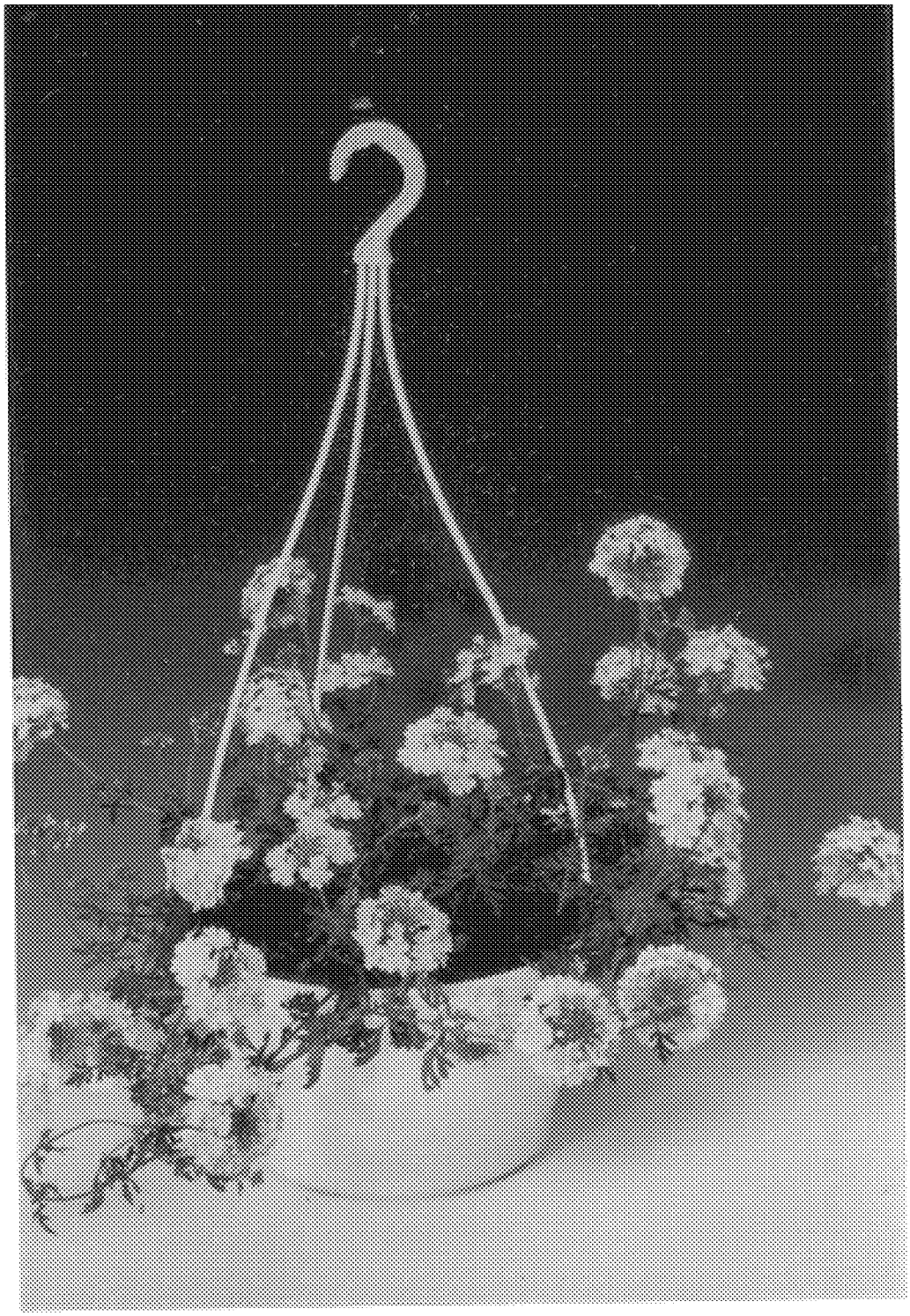
FIG. 1 depicts the spreading and hanging habit of the mature plant, while FIG. 2 provides a more detailed depiction of the blooms and foliage.
Figure 2:
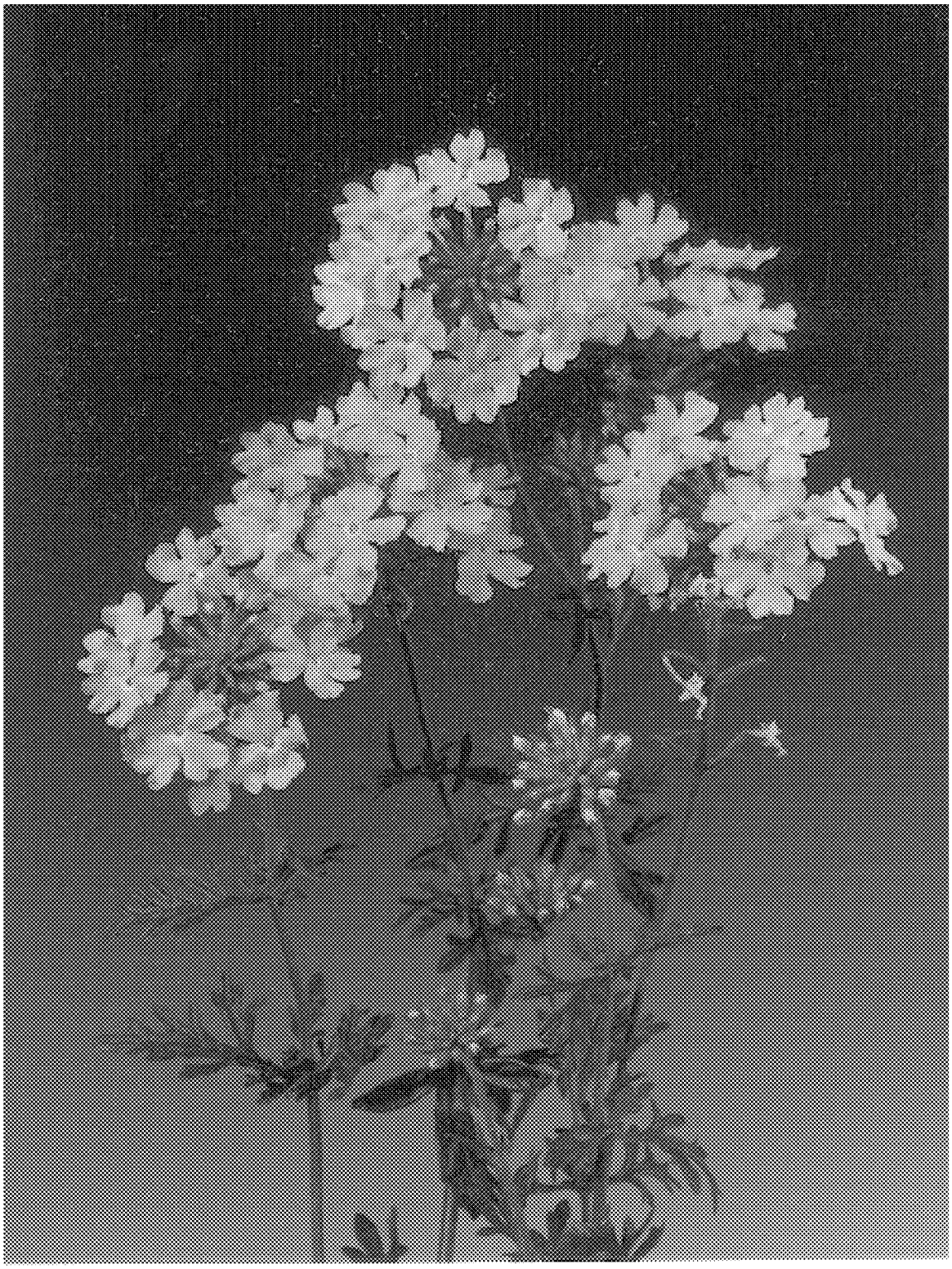

Classification:
*Botanical.*—*Verbena×hybrida.*
Parentage:
*Female parent.*—A seedling named T1183 is one of our seedlings from our T-generation of plants bred in 1991.
*Pollen parent.*—A seedling named R692 is one of our seedlings from our R-generation of plants bred in 1989.
Growth habit: Semi-erect, later spreading.
Plant height: 30–40 cm.
Spreading area of plant: 60–90 cm.
Strength: Very good.
Branching character: After pinching 5–7 breaks occur.
Blooming period: From April until November.

The stem

Diameter: 1.5–2 mm. Cross Section: Tetragonal. Anthocyan pigmentation: Absent. Length of internode: 22–55 mm, depending on the light where the plant is grown.
Pubescence: Pubescence is present.

The Foliage

Phyllotaxis: Opposite.
Shape of blade: Cleft to parted.
Length: 30–45 mm.
Width: 26–38 mm.
Depth of incision: 10–20 mm.
Color:
*Upper side.*—Dark green 141A.
*Lower side.*—Light green 139B.
Pubescence: Some pubescence on both sides of the leaf.
Length of petiole: 10–15 mm.
Color of petiole: Medium green 141B.

The Bud

Peduncle length: 50-80 mm, depending on season.
Size:
*Diameter.*—2 mm.
*Length.*—8–12mm.
Shape: Long.
Color: Medium green 141A.
Sepals:
*Color.*Green 139C.
*Form.*—Upright.

THE FLOWER

Direction: Ascending.
Diameter: 20–24 mm.
Height: 16–18 mm.
Borne: In a cluster.
Form: Flat and symmetrical.
Cluster: Corymb.
Color:
*Upper surface.*—Lavender blue 85A, later 85D.
*Lower surface.*—Light lavender 85D, later 76D.
Eye: A very small (2 mm) green-white eye (155C) is present.
Overlapping of petals: Separate.
Corymb:
*Length.*—40–80 mm, depending on season.
*Diameter.*—30–50 mm.
Calyx: Length of 10–12mm.
Anthocyan pigmentation of Calyx limb: Absent.
No. of flowers per corymb: 30–50.
Flowers in bloom at one time: Maximum 16.
Duration of flowering:
*flower.*—3–5days.
*Inflorescence.*—14–21 days.
Fragrance: A very soft rosy-sweet fragrance.
Reproductive organs: 1pistil, 5stamens. Seeds are formed in a very low frequency.
Physiological and ecological characteristics: Strong resistance to pests and diseases, particularly powdery mildew.

I claim:

1. A new and distinct variety of Verbena plant, substantially as herein illustrated and described, characterized particularly as to novelty by large light lavender blue blooms early flowering, and a growing habit that is first semi-erect but later spreading and hanging.

* * * * *